(12) United States Patent
Misske et al.

(10) Patent No.: US 9,695,136 B2
(45) Date of Patent: Jul. 4, 2017

(54) PROCESS FOR PREPARING HEONONE (METH)ACRYLATE

(71) Applicant: BASF SE, Ludwigshafen am Rhein (DE)

(72) Inventors: Andrea Misske, Speyer (DE); Friederike Fleischhaker, Ludwigshafen (DE); Christoph Fleckenstein, Freigericht-Somborn (DE); Martin Kaller, Mannheim (DE); Ulrik Stengel, Birkenau (DE); Mathieu Blanchot, Lambsheim (DE); Ritesh Nair, Heidelberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/953,854

(22) Filed: Nov. 30, 2015

(65) Prior Publication Data

US 2016/0152580 A1    Jun. 2, 2016

Related U.S. Application Data

(60) Provisional application No. 62/085,660, filed on Dec. 1, 2014.

(51) Int. Cl.
*C07D 263/22* (2006.01)
*C07D 263/38* (2006.01)

(52) U.S. Cl.
CPC ......... *C07D 263/22* (2013.01); *C07D 263/38* (2013.01)

(58) Field of Classification Search
CPC ........................... C07D 263/22; C07D 263/38
See application file for complete search history.

(56) References Cited

U.S. PATENT DOCUMENTS

| | | | | | |
|---|---|---|---|---|---|
| 3,268,485 | A | * | 8/1966 | Hickner | .................. C08F 20/34 526/260 |
| 4,777,265 | A | * | 10/1988 | Merger | ................ C07D 233/32 540/460 |
| 6,147,252 | A | * | 11/2000 | Nakamura | .............. C07C 67/03 560/217 |
| 2010/0280205 | A1 | | 11/2010 | Knebel et al. | |

FOREIGN PATENT DOCUMENTS

| | | | | |
|---|---|---|---|---|
| DE | 2 317 226 A1 | | 10/1974 | |
| DE | WO 2009080380 A2 | * | 7/2009 | ............. C07C 67/03 |
| GB | 980393 A | * | 1/1965 | ........... C07D 207/27 |
| JP | 2010-248310 A | | 11/2010 | |
| WO | WO 2009/080380 A2 | | 7/2009 | |

OTHER PUBLICATIONS

International Search Report issued Jan. 28, 2016 in PCT/EP2015/078090 (with English translation of categories of cited documents).
Zhen Wenyuan, et al., "Preparations and Properties of Functional UV Curable Monomers" Paint & Coatings Industry, vol. 39, No. 8, Aug. 2009, pp. 15-19.

* cited by examiner

*Primary Examiner* — Michael Barker
*Assistant Examiner* — Amanda L Aguirre
(74) *Attorney, Agent, or Firm* — Oblon, McClelland, Maier & Neustadt, L.L.P.

(57) ABSTRACT

A process for preparing heonone (meth)acrylate by transesterification of alkyl (meth)acrylate with heonone.

10 Claims, No Drawings

PROCESS FOR PREPARING HEONONE (METH)ACRYLATE

The invention relates to a process for preparing heonone (meth)acrylate by transesterification of alkyl (meth)acrylate with heonone.

Polymers or copolymers prepared on the basis of branched or linear $C_8$-$C_{24}$-(meth)acrylates are of considerable economic importance in the form of polymer dispersions. The (meth)acrylate of 2-hydroxyethyloxazolidinone (heonone (meth)acrylate) is used for post-crosslinking of polymers. They are employed, for example, as adhesives, lubricants, oilfield chemicals, paints, textile assistants, leather auxiliaries or paper auxiliaries. (Meth)acrylic acid and (meth)acrylate are collective terms for acrylic acid and methacrylic acid and for acrylate and methacrylate, respectively.

Higher alkyl (meth)acrylates can also be obtained by catalytic transesterification of methyl (meth)acrylate with the appropriate long-chain alkanols. This is carried out in the presence of a stabilizer (polymerization inhibitor).

DE 2 317 226 A1 discloses a process for preparing (meth)acrylic esters from a mixture of $C_{10}$-$C_{18}$-alkanols by transesterification of methyl (meth)acrylate in the presence of titanium alkoxide as catalyst and 2,6-di-tert-butylparacresol (TBC) as stabilizer. This is carried out in the presence of activated carbon. After the reaction is complete, water is added, as a result of which the titanium alkoxide is hydrolyzed to titanium hydroxide/oxide which is adsorbed on the activated carbon. The solid is filtered off and the reaction product is subjected to a steam distillation.

WO 2009/080380 discloses a process for preparing methacrylates of $C_6$-$C_{22}$-alcohols by transesterification of methyl (meth)acrylate with the corresponding alcohols in the presence of titanium alkoxide as catalyst. In example 1, methyl methacrylate is reacted with 2-ethylhexanol in the presence of hydroquinone monomethyl ether (MEHQ) as stabilizer and tetraisopropyl titanate as catalyst. Here, an azeotropic mixture of methanol/methyl methacrylate is distilled off. After unreacted methyl methacrylate has been distilled off, the catalyst-comprising 2-ethylhexyl methacrylate is subjected to a pure distillation under reduced pressure (about 30 mbar). This gives 2-ethylhexyl methacrylate having a purity of 99.4%.

In the esterification of (meth)acrylic acid or transesterification of (meth)acrylic esters with long-chain alkanols, by-products can be formed to a not inconsiderable extent by Michael addition. By-products are alkyl esters of di- or oligo(meth)acrylic acid or oxyesters of (meth)acrylic esters of both the starting ester and the product ester. These are high boilers relative to the target product. Alkyl (meth)acrylates of long-chain alkanols can be separated off from these by-products only by vacuum distillation, but above a particular number of carbon atoms in the alkanols reacted separation is only possible in a high vacuum and thus is no longer possible at all in an economical way. Furthermore, the catalyst used and the stabilizer also have to be separated off from the product. If the boiling point of the target product is not too high, a final pure distillation of the target product is generally carried out.

Heonone (meth)acrylate (2-hydroxyethyloxazolidinone (meth)acrylate) is used for the post-crosslinking of polymers, for example of polyacrylates for superabsorbents. Heonone acrylate is of particular importance. Heonone acrylate has the following structural formula:

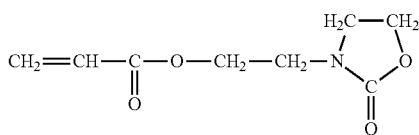

In the preparation of heonone (meth)acrylate by transesterification of alkyl (meth)acrylate with heonone (2-hydroxyethyloxazolidinone), the formation of Michael adducts as by-products of the transesterification reaction is a particular problem.

It is an object of the invention to provide a process for preparing heonone (meth)acrylate by transesterification of alkyl (meth)acrylate with heonone, in which by-products are formed to only a small extent.

The object is achieved by a process for preparing heonone (meth)acrylate by transesterification of alkyl (meth)acrylate with heonone, which comprises the steps:

(i) reaction of alkyl (meth)acrylate with heonone in the presence of a catalyst comprising titanium(IV) or zirconium(IV) and a stabilizer in the presence of an entrainer which forms an azeotrope with the alcohol bound in the alkyl (meth)acrylate, (ii) continuous removal by distillation of the azeotrope of entrainer and alcohol, with steps (i) and (ii) being carried out simultaneously until heonone has been essentially completely reacted, (iii) addition of water to the product mixture comprising heonone (meth)acrylate obtained in steps (i) and (ii) and removal of hydrolyzates of the catalyst comprising titanium(IV) or zirconium(IV), (iv) distillation of unreacted alkyl (meth)acrylate and entrainer from the product mixture, (v) distillation of water from the product mixture, with step (iv) also being able to be carried out before step (iii) and steps (iv) and (v) also being able to be carried out in a distillation step, wherein steps (i) and (ii) are carried out in the presence of an inorganic or organic acid.

It has surprisingly been found that heonone (meth)acrylate is formed quite predominantly by transesterification of alkyl (meth)acrylate with heonone in the presence of a catalyst comprising titanium(IV) or zirconium(IV) when the reaction is carried out in the presence of an inorganic or organic acid. Michael adducts are not formed to an appreciable extent.

Michael adducts of alkyl (meth)acrylate are generally formed in amounts of <0.5% by weight, preferably <0.1% by weight, based on the heonone (meth)acrylate formed. In general, a heonone (meth)acrylate having a by-product content of not more than 2% by weight is obtained after step (v).

For the purposes of the present invention, Michael adducts are the 1,4-addition products of the alcohol heonone with the starting monomer alkyl (meth)acrylate or target monomer heonone (meth)acrylate. These are also referred to as oxy esters. By-products encompass not only the Michael adducts with alkyl (meth)acrylate but also further compounds which are not the target product heonone (meth)acrylate. The content of by-products in the product obtained after step (v) is preferably <2% by weight. In addition, the product obtained after step (v) can comprise unreacted heonone. This does not represent a by-product. In general, the heonone content of the product obtained after step (v) is up to 3% by weight, preferably up to 2% by weight. In addition, the product obtained after step (v) can still comprise traces of entrainer, alkyl (meth)acrylate and water. These likewise do not represent by-products and can be comprised in total amounts of up to 2% by weight, preferably up to 1% by weight, in the product obtained after step (v).

The amount of all secondary components (including by-products, heonone, entrainer, alkyl (meth)acrylate, water) in the product obtained after step (v) is generally up to 6% by weight, preferably up to 4% by weight.

Suitable alkyl (meth)acrylates are the $C_1$-$C_4$-alkyl (meth) acrylates. Methyl (meth)acrylate or ethyl (meth)acrylate are generally used, with the transesterification reaction liberating methanol or ethanol as alcohols.

The reaction of alkyl (meth)acrylate with heonone occurs in the presence of a catalyst comprising titanium(IV) or zirconium(IV). Suitable catalysts comprising titanium(IV) or zirconium(IV) are the Ti(IV) or Zr(IV) tetraalkoxides of linear or branched $C_1$-$C_6$-alcohols, preferably tetraisopropoxides, tetrabutoxides and the metallate of the starting alcohol used or mixtures thereof. Metallates substituted by different alcohols or acetyl acetonate are also possible.

Steps (i) and (ii) are additionally carried out in the presence of an inorganic or organic acid. Particularly suitable inorganic acids are phosphoric acid, sulfuric acid, nitric acid, hydrochloric acid, with phosphoric acid and sulfuric acid being very particularly useful. Particularly suitable organic acids are acrylic acid, methacrylic acid and acetic acid. The acid is generally used in amounts of from 0.01 to 5% by weight, preferably from 0.1 to 1% by weight, based on the total amount of the components comprised in the reaction mixture.

The reaction of alkyl (meth)acrylate with heonone is also carried out in the presence of one or more stabilizers (polymerization inhibitors). Suitable stabilizers can, for example, be N-oxides (nitroxyl or N-oxyl radicals, i.e. compounds which have at least one >N—O group), e.g. 4-hydroxy-2,2,6,6-tetramethylpiperidin-N-oxyl, 4-oxo-2,2,6,6-tetramethylpiperidin-N-oxyl, 4-acetoxy-2,2,6,6-tetramethylpiperidin-N-oxyl, 2,2,6,6-tetramethylpiperidin-N-oxyl, bis(1-oxyl-2,2,6,6-tetramethylpiperidin-4-yl) sebacate, 4,4', 4"-tris(2,2,6,6-tetramethylpiperidin-N-oxyl) phosphite or 3-oxo-2,2,5,5-tetramethylpyrrolidin-N-oxyl; monobasic or polybasic phenols which optionally have one or more alkyl groups, e.g. alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones such as hydroquinone, hydroquinone monomethyl ether, 2-methylhydroquinone or 2,5-di-tert-butylhydroquinone; hydroxyphenols such as catechol (1,2-dihydroxybenzene) or benzoquinone; aminophenols such as p-aminophenol; nitrosophenols such as p-nitrosophenol; alkoxyphenols such as 2-methoxyphenol (guaiacol, catechol monomethyl ether), 2-ethoxyphenol, 2-isopropoxyphenol, 4-methoxyphenol (hydroquinone monomethyl ether), mono- or di-tert-butyl-4-methoxyphenol; tocopherols such as α-tocopherol and also 2,3-dihydro-2,2-dimethyl-7-hydroxybenzofuran (2,2-dimethyl-7-hydroxycoumaran), aromatic amines such as N,N-diphenylamine or N-nitrosodiphenylamine; phenylenediamines such as N,N'-dialkyl-p-phenylenediamine, where the alkyl radicals can be identical or different and in each case independently have from 1 to 4 carbon atoms and can be linear or branched, e.g. N,N'-dimethyl-p-phenylenediamine or N,N'-diethyl-p-phenylenediamine, hydroxylamines such as N,N-diethylhydroxylamine, imines such as methylethylimine or methylene violet, sulfonamides such as N-methyl-4-toluenesulfonamide or N-tert-butyl-4-toluenesulfonamide, oximes such as aldoximes, ketoximes or amidoximes, e.g. diethyl ketoxime, methyl ethyl ketoxime or salicylaldoxime, phosphorus-comprising compounds such as triphenylphosphine, triphenyl phosphite, triethyl phosphite, hypophosphorous acid or alkyl esters of phosphorous acids; sulfur-comprising compounds such as diphenyl sulfide or phenothiazine; metal salts such as copper or manganese, cerium, nickel, chromium salts, for example chlorides, sulfates, salicylates, tosylates, acrylates or acetates, e.g. copper acetate, copper(II) chloride, copper salicylate, cerium(III) acetate or cerium(III) ethylhexanoate, or mixtures thereof.

Preference is given to hydroquinone, hydroquinone monomethyl ether, phenothiazine, 4-hydroxy-2,2,6,6-tetramethylpiperidin-N-oxyl, 4-oxo-2,2,6,6-tetramethylpiperidin-N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol and 2-methyl-4-tert-butylphenol.

Particular preference is given to hydroquinone monomethyl ether (MEHQ).

Advantageously, oxygen can additionally be used as polymerization inhibitor.

For further stabilization, an oxygen-comprising gas, preferably air or a mixture of air and nitrogen (lean air) can be present.

The transesterification reaction (steps (i) and (ii)) is generally carried out at a temperature of from 60 to 140° C., preferably from 70 to 110° C. Here, an azeotrope of entrainer and alcohol is continuously distilled off.

Suitable entrainers which form an azeotropically boiling mixture with methanol or ethanol are firstly methyl acrylate and methyl methacrylate and also ethyl acrylate and ethyl (meth)acrylate themselves. Suitable separate entrainers are, inter alia, cyclohexane, methylcyclohexane, benzene, toluene, hexanes and heptanes and mixtures thereof. Preference is given to methyl acrylate, methyl methacrylate, ethyl acrylate and ethyl (meth)acrylate and also mixtures of these with n-heptane and cyclohexane. For the present purposes, the term entrainer comprises the starting material itself and optionally a separate solvent which is additionally used.

In a preferred embodiment, no separate solvent is used as entrainer. In this case, the starting material alkyl (meth) acrylate itself acts as entrainer.

The entrainer can subsequently be replenished again in the reactor. For this purpose, the azeotropic mixture of alcohol and entrainer is, in a preferred embodiment, distilled off via a suitable column, stirred with water in a mixing vessel and then transferred to a phase separator, with the alcohol, generally methanol or ethanol, dissolving in water and the organic phase separating out as upper layer. The organic phase is preferably returned via the top of the column to the reaction mixture and thus circulated except for small losses. However, as an alternative, fresh entrainer can also be introduced and a work-up of the entrainer/alcohol mixture can be carried out in a separate step or the replenishment of the entrainer can be entirely or partly omitted.

In general, alkyl (meth)acrylate is used in a stoichiometric excess. The excess of methyl (meth)acrylate per hydroxyl group to be esterified is preferably from 5 to 200 mol %, particularly preferably from 5 to 100 mol %, in particular from 5 to 50 mol %.

The catalyst is used in a concentration of 0.1-10 mol %, preferably in a concentration of from 0.1 to 5 mol %, based on the amount of heonone.

The transesterification can be carried out at atmospheric pressure or else at superatmospheric pressure or subatmospheric pressure. In general, it is carried out at from 300 to 1000 mbar, preferably 800-1000 mbar (atmospheric pressure=1000 mbar). The reaction time is generally from 1 hour to 24 hours, preferably from 3 to 18 hours, particularly preferably from 6 to 12 hours. The transesterification (steps (i) and (ii)) can be carried out continuously, for example in a cascade of stirred vessels, or batchwise.

The reaction can be carried out in all reactors suitable for such a reaction. Such reactors are known to those skilled in the art. The reaction is preferably carried out in a stirred tank reactor.

To mix the batch, it is possible to use any methods, e.g. stirring devices. Mixing can also be effected by introduction of a gas, preferably an oxygen-containing gas.

The removal of the alcohol formed, in general methanol or ethanol, is carried out continuously or stepwise in a manner known per se by azeotropic distillation in the presence of an entrainer. In addition, methanol can also be removed by stripping with a gas.

In a preferred embodiment, the alcohol is separated off from the azeotrope of entrainer and alcohol distilled off in step (ii) by scrubbing with water and the entrainer is recirculated to the reaction vessel.

Steps (i) and (ii) are carried out until the heonone used has been essentially completely reacted. This is the case when heonone has been reacted to an extent of 95%, preferably 98%, particularly preferably 99%.

Steps (iii) and (iv), which can also be carried out in the reverse order, are subsequently carried out.

In step (iii), water is added to the product mixture comprising heonone (meth)acrylate, as a result of which the catalyst comprising titanium(IV) or zirconium(IV) is hydrolyzed to the corresponding hydroxide. The sparingly soluble hydrolyzate is subsequently separated off, e.g. by filtration or centrifugation.

The filtration can, for example, be carried out using a pressure filter. From a process engineering point of view, all filtration methods and apparatuses known per se, e.g. those described in Ullmann's Encyclopedia of Industrial Chemistry, 7th ed, 2013 Electronic Release, Chapter: Filtration, 1. Fundamentals and Filtration 2. Equipment, can be used for filtration in the process of the invention. For example, these can be candle filters, filter presses, plate pressure filters, bag filters or drum filters. Preference is given to using candle filters or plate pressure filters. Filtration can be carried out with or without filter aids. Suitable filter aids are filter aids based on kieselguhr, perlite and cellulose.

Suitable centrifuges and also separators are known to an expert. From a process engineering point of view, all centrifugation methods and apparatuses known per se, e.g. those described in Ullmann's Encyclopedia of Industrial Chemistry, 7th ed, 2013 Electronic Release, Chapter: Centrifuges, Filtering and Centrifuges, Sedimenting, can be used for centrifugation in the process of the invention.

In a preferred embodiment, unreacted alkyl (meth)acrylate and also water are subsequently distilled off from the product mixture in the distillation steps (iv) and (v). This distillation is generally carried out at a temperature of from 40 to 100° C., preferably from 60 to 80° C., and a variable pressure of from 10 to 700 mbar. In addition, these components can also be removed by stripping with a gas, preferably an oxygen-containing gas.

If no separate entrainer is used, the steps (iv) and (v) are preferably carried out in a joint distillation step. If a separate entrainer is used, then step (iv) is preferably carried out before step (iii).

The removal by distillation is, for example, carried out in a stirred vessel having double-walled heating and/or internal heating coils under reduced pressure.

Of course, the distillation can also be carried out in a falling film evaporator or thin film evaporator. For this purpose, the reaction mixture is passed, preferably with repeated circulation, through the apparatus under reduced pressure, for example at from 20 to 700 mbar, preferably from 30 to 500 mbar, particularly preferably from 50 to 150 mbar, and a temperature of from 40 to 80° C.

An inert gas, preferably an oxygen-containing gas, particularly preferably air or a mixture of air and nitrogen (lean air) can advantageously be fed into the distillation apparatus, for example from 0.1 to 1 $m^3/m^3h$, preferably from 0.2 to 0.8 $m^3/m^3h$ and particularly preferably from 0.3 to 0.7 $m^3/m^3h$, based on the volume of the reaction mixture.

After carrying out steps (iii), (iv) and (v), a product having the above-described purity remains as bottom product.

The invention is illustrated by the following examples.

EXAMPLES

Example 1

Heonone Acrylate by Transesterification Using a Titanium-comprising Catalyst

Ethyl acrylate (1500 g), MeHQ (2 g), acrylic acid (2.5 g) and heonone (694 g) are placed in a 4 l flange reactor provided with superposed column (Montz A3-500 packing), condenser, liquid distributor, anchor stirrer and lean air inlet and heated up while introducing lean air and stirring. To remove water, ethyl acrylate is distilled off and replaced by fresh ethyl acrylate. Titanium tetraisopropoxide (14 g) is introduced at a temperature at the bottom of 79° C. and the mixture is heated up further to a temperature at the bottom of 102° C. After commencement of boiling, a reflux ratio of 5:2 is established. Ethyl acrylate is introduced a little at a time in amounts which correspond to the distillate. After 5.5 hours, 20 g of catalyst are additionally introduced. The temperature at the bottom rises to 104° C. during the course of the reaction. Bottom and distillate samples are taken at regular intervals in order to observe the course of the reaction. After a reaction time of 17 hours, GC (% by area) indicates a content of 98.8% of heonone acrylate and 1.2% of residual alcohol (ethyl acrylate left out of the calculation). 150 ml of water are added, the reaction mixture is filtered through a sand-filled frit and evaporated under reduced pressure.

After clear filtration, the product is obtained in a yield of 830 g and a purity of 96% (GC-% by area). Two unknown by-products in a total amount of 1.7% but no Michael adduct can be seen in the GC. The residual alcohol content is 2.2%.

Example 2

Heonone Acrylate by Transesterification Using a Titanium-comprising Catalyst

Ethyl acrylate (1500 g), MeHQ (2 g), phosphoric acid 85% (12 g) and heonone (694 g) are placed in a 4 flange reactor provided with superposed column (Montz A3-500 packing), condenser, liquid distributor, anchor stirrer and lean air inlet and heated up while introducing lean air and stirring. To remove water, ethyl acrylate is distilled off and replaced by fresh ethyl acrylate. Titanium tetraisopropoxide (14 g) is introduced at a temperature at the bottom of 76° C. and the mixture is heated up further to a temperature at the bottom of 103° C. After commencement of boiling, a reflux ratio of 5:2 is established. After 4 hours, 14 g of catalyst are additionally introduced. The temperature at the bottom rises to 104° C. during the course of the reaction. Bottom and distillate samples are taken at regular intervals in order to observe the course of the reaction. After a reaction time of 16.5 hours, GC (% by area) indicates a content of 97% of heonone acrylate and 0.8% of residual alcohol (ethyl acrylate left out of the calculation). 150 ml of water are added, the reaction mixture is filtered through a sand-filled frit and a Seitz filter.

The reaction mixture is concentrated under reduced pressure. The product is obtained in an amount of 787 g and a purity of 95.4% (GC-% by area). An unknown by-product in a total amount of 1.1% but no Michael adduct can be seen in the GC. The residual alcohol content is 1.6%, and the ethyl acrylate content is 1.7%.

Comparative Example 1

Heonone Acrylate by Transesterification Using a Titanium-comprising Catalyst

Ethyl acrylate (500 g), MeHQ (0.23 g), PTZ (0.02 g) and heonone (150 g) are placed in a 0.75 flange reactor provided with superposed column, condenser, liquid distributor, anchor stirrer and lean air inlet and heated up by means of a bath temperature of 80° C. while introducing lean air and stirring. To remove water, ethyl acrylate is distilled off and replaced by fresh ethyl acrylate. Titanium tetraisopropoxide (5 g) is introduced and the mixture is heated up further to a temperature at the bottom of 97° C. A vacuum of 900 mbar is applied, and this is increased to 970 mbar during the course of the reaction. After the commencement of boiling, a reflux ratio of 10:1 is established. The temperature at the bottom rises to 105° C. during the course of the reaction. Bottom and distillate samples are taken at regular intervals in order to observe the course of the reaction. After a reaction time of 5 hours, GC (% by area) indicates a content of 43% of heonone acrylate, 45% of Michael adduct (Michael adduct of the alcohol with ethyl acrylate identified via GC-MS) and 12% of residual alcohol (ethyl acrylate left out of the calculation). The experiment is stopped.

Comparative Example 2

Heonone Acrylate by Transesterification Using a Zirconium-comprising Catalyst

Ethyl acrylate (1500 g), MeHQ (1.97 g) and heonone (694 g) are placed in a 4 l flange reactor provided with superposed column (Montz A3-500 packing), condenser, liquid distributor, anchor stirrer and lean air inlet and heated up to a temperature at the bottom of 45° C. while introducing lean air and stirring. Zr(IV) acetylacetonate (12.2 g) is introduced and the mixture is heated further to a temperature at the bottom of 76-80° C. at a pressure of 930 mbar. The reflux ratio is varied from 10:1 to 5:2. Bottom and distillate samples are taken at regular intervals in order to observe the course of the reaction. After a reaction time of 11 hours, GC (% by area) indicates a content of 15% of heonone acrylate, 20% of Michael adduct (Michael adduct of the alcohol with ethyl acrylate identified via GC-MS), a total of >3% of unknown by-products and 60% of residual alcohol (ethyl acrylate left out of the calculation). The experiment is stopped. The by-product is the Michael adduct of the alcohol with ethyl acrylate.

The invention claimed is:

1. A process for preparing heonone (meth)acrylate by transesterification of alkyl (meth)acrylate with heonone, which comprises the steps:
   (i) reaction of alkyl (meth)acrylate with heonone in the presence of a catalyst comprising titanium(IV) or zirconium(IV) and a stabilizer in the presence of an entrainer which forms an azeotrope with the alcohol produced from the alkyl (meth)acrylate,
   (ii) continuous removal by distillation of the azeotrope of entrainer and alcohol, with steps (i) and (ii) being carried out simultaneously until heonone has essentially completely reacted,
   (iii) addition of water to the product mixture comprising heonone (meth)acrylate obtained in steps (i) and (ii) and removal of the hydrolyzate of the catalyst comprising titanium(IV) or zirconium(IV) by filtration,
   (iv) distillation of unreacted alkyl (meth)acrylate and entrainer from the product mixture, and
   (v) distillation of water from the product mixture,
   with step (iv) also being able to be carried out before step (iii) and steps (iv) and (v) also being able to be carried out in a distillation step,
   wherein steps (i) and (ii) are carried out in the presence of an inorganic or organic acid.

2. The process according to claim 1, wherein the entrainer is the alkyl (meth)acrylate.

3. The process according to claim 1, wherein the entrainer is a separate solvent different from alkyl (meth)acrylate.

4. The process according to claim 3, wherein the entrainer is selected from the group consisting of n-heptane and cyclohexane.

5. The process according to claim 1, wherein steps (iv) and (v) are carried out in a joint distillation step.

6. The process according to claim 1, wherein the alkyl (meth)acrylate is methyl or ethyl (meth)acrylate.

7. The process according to claim 1, wherein the catalyst comprises titanium(IV) tetraisopropoxide.

8. The process according to claim 1, wherein the stabilizer is methylhydroquinone.

9. The process according to claim 1, wherein the alcohol is separated off from the azeotrope of entrainer and alcohol, distilled off in step (ii), by scrubbing with water and the entrainer is recirculated to the reaction vessel.

10. The process according to claim 1, wherein a heonone (meth)acrylate having a by-product content of <2% by weight is obtained after step (v).

* * * * *